(12) United States Patent
Dong et al.

(10) Patent No.: US 8,768,466 B2
(45) Date of Patent: Jul. 1, 2014

(54) METHOD AND APPARATUS TO TREND AND OPTIMIZE AN IMPLANTABLE MEDICAL DEVICE USING A PATIENT MANAGEMENT SYSTEM

(75) Inventors: Yanting Dong, Shoreview, MN (US); Xuan Wei, Plymouth, MN (US); Ankur Garg, Minneapolis, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1161 days.

(21) Appl. No.: 12/249,856

(22) Filed: Oct. 10, 2008

(65) Prior Publication Data

US 2009/0105777 A1 Apr. 23, 2009

Related U.S. Application Data

(60) Provisional application No. 60/979,742, filed on Oct. 12, 2007.

(51) Int. Cl.
| | | |
|---|---|---|
| *A61N 1/00* | (2006.01) | |
| *A61N 1/372* | (2006.01) | |
| *G06F 19/00* | (2011.01) | |
| *A61N 1/365* | (2006.01) | |

(52) U.S. Cl.
CPC ............ *A61N 1/365* (2013.01); *A61N 1/37211* (2013.01); *A61N 1/36585* (2013.01); *A61N 1/37264* (2013.01); *A61N 1/37282* (2013.01); *G06F 19/3481* (2013.01); *G06F 19/3418* (2013.01)
USPC .................................. 607/30; 607/9; 607/27

(58) Field of Classification Search
CPC ........... A61N 1/37247; A61N 1/37252; A61N 1/37264

USPC ............................................ 607/27, 9, 48, 30
See application file for complete search history.

(56) References Cited

U.S. PATENT DOCUMENTS

| 5,487,752 A | 1/1996 | Salo et al. |
| 5,509,927 A | 4/1996 | Epstein et al. |

(Continued)

FOREIGN PATENT DOCUMENTS

| EP | 1350539 A1 | 10/2003 |
| EP | 1484083 A1 | 12/2004 |

(Continued)

OTHER PUBLICATIONS

"U.S. Appl. No. 11/614,578, Final Office Action mailed Mar. 3, 2011", 8 pgs.

(Continued)

*Primary Examiner* — Christopher D Koharski
*Assistant Examiner* — Philip Edwards
(74) *Attorney, Agent, or Firm* — Schwegman, Lundberg & Woessner, P.A.

(57) ABSTRACT

A remote external interface for an implantable cardiac function management device is configured to be communicatively coupled to the implantable cardiac function management device via a network to a local external interface and via telemetry between the local external interface and the implantable cardiac function management device. The remote external interface includes a communication circuit and a processor circuit. The communication circuit is configured to communicate with the implantable cardiac function management device. The processor circuit is configured to perform an analysis of physiologic data received from the implantable cardiac function management device in response to operation of the implantable cardiac function management device using a plurality of therapy control parameter sets. The processor circuit can be further configured to select a particular therapy control parameter set using the analysis.

29 Claims, 11 Drawing Sheets

(56) References Cited

U.S. PATENT DOCUMENTS

| | | | |
|---|---|---|---|
| 5,891,176 | A | 4/1999 | Bornzin |
| 6,522,923 | B1 | 2/2003 | Turcott |
| 6,792,310 | B1 | 9/2004 | Turcott et al. |
| 6,882,883 | B2 | 4/2005 | Condie et al. |
| 6,978,182 | B2 | 12/2005 | Mazar et al. |
| 7,110,818 | B2 | 9/2006 | Anderson et al. |
| 7,184,835 | B2 | 2/2007 | Kramer et al. |
| 7,200,435 | B2 | 4/2007 | Ricci et al. |
| 7,231,248 | B2 | 6/2007 | Kramer et al. |
| 7,542,803 | B2 | 6/2009 | Heruth et al. |
| 2003/0097158 | A1 | 5/2003 | Belalcazar |
| 2004/0098065 | A1* | 5/2004 | Hagglof et al. ............. 607/48 |
| 2004/0106960 | A1 | 6/2004 | Siejko et al. |
| 2005/0038477 | A1* | 2/2005 | Kramer et al. ............. 607/9 |
| 2005/0043767 | A1 | 2/2005 | Belalcazar |
| 2005/0102002 | A1 | 5/2005 | Salo et al. |
| 2005/0131469 | A1 | 6/2005 | Cohen |
| 2005/0209511 | A1 | 9/2005 | Heruth et al. |
| 2005/0216064 | A1 | 9/2005 | Heruth et al. |
| 2006/0025830 | A1 | 2/2006 | Freeberg |
| 2006/0106433 | A1 | 5/2006 | Mazar et al. |
| 2006/0111751 | A1 | 5/2006 | Cazares |
| 2007/0135854 | A1 | 6/2007 | Kramer et al. |
| 2007/0156187 | A1 | 7/2007 | Ricci et al. |
| 2007/0162080 | A1 | 7/2007 | Brockway et al. |
| 2008/0154323 | A1 | 6/2008 | Sathaye et al. |
| 2009/0254139 | A1 | 10/2009 | Bjorling |

FOREIGN PATENT DOCUMENTS

| | | | |
|---|---|---|---|
| EP | 1849412 | B1 | 3/2009 |
| WO | WO-03/037428 | A2 | 5/2003 |
| WO | WO-2005/122902 | A1 | 12/2005 |
| WO | WO-2008/079347 | A1 | 7/2008 |

OTHER PUBLICATIONS

"U.S. Appl. No. 11/614,578, Non-Final Office Action mailed Apr. 29, 2010", 8 pgs.

"U.S. Appl. No. 11/614,578, Response filed May 18, 2011 to Final Office Action mailed Mar. 3, 2011", 10 pgs.

"U.S. Appl. No. 11/614,578, Response filed Jul. 29, 2010 to Non Final Office Action mailed Apr. 29, 2010", 9 pgs.

"U.S. Appl. No. 11/614,578, Final Office Action mailed Nov. 16, 2009", 7 pgs.

"U.S. Appl. No. 11/614,578, Non-Final Office Action mailed Mar. 31, 2009", 8 pgs.

"U.S. Appl. No. 11/614,578, Examiner Interview Summary mailed Jun. 30, 2009", 2 pgs.

"U.S. Appl. No. 11/614,578, Response filed Feb. 15, 2010 to Final Office Action mailed Nov. 16, 2009", 7 pgs.

"U.S. Appl. No. 11/614,578, Response filed Mar. 2, 2009 to Restriction Requirement mailed Jan. 29, 2009", 5 pgs.

"U.S. Appl. No. 11/614,578, Response filed Jun. 30, 2009 to Non-Final Office Action mailed Mar. 31, 2009", 8 pgs.

"U.S. Appl. No. 11/614,578, Restriction Requirement mailed Jan. 29, 2009", 5 pgs.

"International Application Serial No. PCT/US2007/026191, Written Opinion mailed on May 28, 2008", 3 pgs.

"International Application Serial No. PCT/US2007/026191. International Search Report mailed on May 28, 2008", 5 pgs.

"U.S. Appl. No. 11/614,578, Examiner Interview Summary mailed Nov. 18, 2010", 4 pgs.

"U.S. Appl. No. 11/614,578, Non Final Office Action mailed Dec. 17, 2013", 10 pgs.

* cited by examiner

METHOD AND APPARATUS TO TREND AND OPTIMIZE AN IMPLANTABLE MEDICAL DEVICE USING A PATIENT MANAGEMENT SYSTEM

CLAIM OF PRIORITY

Benefit of priority is hereby claimed to U.S. patent application Ser. No. 11/614,578, filed Dec. 21, 2006 and entitled "METHOD AND APPARATUS TO IMPLEMENT MULTIPLE PARAMETER SETS IN AN IMPLANTABLE DEVICE", and U.S. Provisional Application No. 60/979,742, filed Oct. 12, 2007 and entitled "METHOD AND APPARATUS TO TREND AND OPTIMIZE AN IMPLANTABLE MEDICAL DEVICE USING A PATIENT MANAGEMENT SYSTEM", and PCT Application No. PCT/US2007/026191, filed Dec. 21, 2007 and entitled "IMPLANTABLE DEVICE WITH MULTIPLE PARAMETER SETS", which applications are incorporated herein by reference.

TECHNICAL FIELD

This document relates generally to cardiac rhythm management (CRM) systems and particularly, but not by way of limitation, to a method and apparatus to trend and adjust an implantable medical device using a patient management system.

BACKGROUND

In a normal heart, the sinoatrial node, the heart's predominant natural pacemaker, generates electrical impulses, called action potentials, that propagate through an electrical conduction system to the atria and then to the ventricles of the heart to excite the myocardial tissues. The atria and ventricles contract in the normal atrio-ventricular sequence and synchrony to result in efficient blood-pumping functions indicated by a normal hemodynamic performance. These intrinsic action potentials can be sensed on a surface electrocardiogram (i.e., a "surface ECG signal") obtained from electrodes placed on the patient's skin, or from electrodes implanted within the patient's body (i.e., an "electrogram signal"). The surface ECG and electrogram waveforms, for example, include artifacts associated with atrial depolarizations ("P-waves") and those associated with ventricular depolarizations ("QRS complexes").

When people have irregular cardiac rhythms, referred to as cardiac arrhythmias, or poor spatial coordination of heart contractions, diminished blood circulation may result. For such persons, cardiac rhythm management (CRM) systems may be used to improve these conditions. CRM systems include, among other things, pacemakers which deliver timed sequences of low energy electrical stimuli, called pace pulses, to the heart. By properly timing the delivery of pace pulses, the heart can be induced to contract in proper rhythm, improving efficiency. Another type of CRM system includes defibrillators that are capable of delivering higher energy electrical stimuli to the heart. Such defibrillators include cardioverters, which synchronize the delivery of such stimuli to sensed intrinsic heart activity signals. Defibrillators are often used to treat patients with tachyarrhythmias, which can be thought of as abnormal heart rhythms characterized by a rapid heart rate. Fibrillation is a form of tachyarrhythmia further characterized by an irregular heart rhythm.

Upon implantation, a CRM device is programmed to perform in response to detected electrical or mechanical disturbances within the heart. How the device is programmed may have a direct impact upon patient outcome. When the device is first implanted, a caregiver may rely upon historical data to determine how to set the programming parameters to be used until the next follow-up appointment, during which time results may be measured and recorded. After a specified period of time, the patient returns for a follow-up visit with the caregiver, the results are evaluated, and the device is re-programmed, if appropriate.

OVERVIEW

The present inventors have recognized that the iterative nature of the programming process, coupled with the large number of variables which may impact the functionality of the heart may delay finding an improved or optimized programmed parameter set. For these and other reasons, the present inventors have recognized a need for improved techniques of programming parameter sets.

Example 1 describes an example of an apparatus comprising a remote external interface for an implantable cardiac function management device, configured to be communicatively coupled to the implantable cardiac function management device via a network to a local external interface and via telemetry between the local external interface and the implantable cardiac function management device, the remote external interface comprising a communication circuit, configured to communicate with the implantable cardiac function management device; and a processor circuit, configured to perform an analysis of physiologic data received from the implantable cardiac function management device in response to operation of the implantable cardiac function management device using a plurality of therapy control parameter sets, the processor circuit configured to select a particular therapy control parameter set using the analysis.

In Example 2, the apparatus of Example 1 optionally includes the implantable cardiac function management device.

In Example 3, the apparatus of Examples 1-2 optionally includes the local external interface.

In Example 4, the apparatus of Examples 1-3 optionally includes an external sensor device.

In Example 5, the apparatus of Examples 1-4 optionally includes the processor circuit being located in the network.

In Example 6, the apparatus of Examples 1-5 optionally includes the remote external interface configured to program the implantable cardiac function management device with one or more of the particular therapy control parameter set and a particular physiological response to store.

In Example 7, the apparatus of Examples 1-6 optionally includes the remote external interface configured to program the implantable cardiac function management device with an original therapy control parameter set or a default therapy control parameter set.

In Example 8, the apparatus of Examples 1-7 optionally includes the local external interface, the network, or the remote external interface configured to suggest to a third party the particular therapy control parameter set to program into the implantable cardiac function management device.

In Example 9, the apparatus of Examples 1-8 optionally includes the suggestion being based on at least one of an analysis of an aggregation of historic patient data or device performance data.

In Example 10, the apparatus of Examples 1-9 optionally includes the remote external interface configured to receive information about at least one of the plurality of therapy control parameter sets from a third party.

In Example 11, the apparatus of Examples 1-10 optionally includes the remote external interface configured to receive from a third party at least one of a selection of the particular therapy control parameter set or a value for a physiological parameter.

In Example 12, the apparatus of Examples 1-11 optionally includes the processor configured to perform an analysis of at least one of device performance data or patient feedback data.

In Example 13, the apparatus of Examples 1-12 optionally includes at least one of the therapy control parameter sets including at least one of an AV delay parameter, a VV offset parameter, a rate response parameter, a tachy detection parameter, a tachy therapy parameter, a pacing amplitude parameter, or a neural stimulation parameter.

In Example 14, the apparatus of Examples 1-13 optionally includes the processor configured to perform the analysis of physiologic data that includes at least one of a heart rate variability, a peripheral pressure, a blood pressure, a body weight, an activity log, a tachy conversion efficacy, a respiration rate, a posture indicator, a hemodynamic response parameter, an electrocardiogram, or a percentage of A/V pacing.

In Example 15, the apparatus of Examples 1-14 optionally includes the remote external interface configured to communicate with the implantable cardiac function management device during a real time communication session.

In Example 16, the apparatus of Examples 1-15 optionally includes the processor circuit configured to adjust therapy control parameter sets using the analysis of the physiologic data.

In Example 17, the apparatus of Examples 1-16 optionally includes the adjustment of the therapy control parameter sets uses at least one of a gradient search, an evolution algorithm, a simulated annealing method, a simplex algorithm, or a simplex algorithm.

In Example 18, a process includes receiving over a network physiologic data from an implantable cardiac function management device, the physiologic data resulting from operation of the implantable cardiac function management device using a plurality of therapy control parameter sets; analyzing the physiologic data; and selecting a particular therapy control parameter set using the analysis.

In Example 19, the process of Example 18 optionally includes programming the implantable cardiac function management device with the particular therapy control parameter set.

In Example 20, the process of Examples 18-19 optionally includes programming the implantable cardiac function management device with an original therapy control parameter set or a default therapy control parameter set.

In Example 21, the process of Examples 18-20 optionally includes providing to a third party a suggestion of the particular therapy control parameter set to program into the implantable cardiac function management device.

In Example 22, the process of Examples 18-21 optionally includes automatically adjusting the particular therapy control parameter set or a particular therapy control parameter and automatically programming the adjusted particular therapy control parameter set or the particular therapy control parameter into the implantable cardiac function management device.

In Example 23, the process of Examples 18-22 optionally includes receiving, at the remote external interface, from a third party, the one or more therapy control parameter sets.

In Example 24, the process of Examples 18-23 optionally includes receiving, at the remote external interface, an interval range for at least one parameter in the therapy control parameter sets, a time interval that the cardiac function management device is configured to operate with at least one of the therapy control parameter sets, or a value for a physiological parameter.

In Example 25, the process of Examples 18-24 optionally includes communicating with the implantable cardiac function management device in real time.

In Example 26, the process of Examples 18-25 optionally includes adjusting parameter sets using the analysis of the physiologic data.

In Example 27, the process of Examples 18-26 optionally includes adjusting the parameter search space using at least one of a gradient search, an evolution algorithm, a simulated annealing method, or a simplex algorithm.

In Example 28, an apparatus includes means for receiving over a network physiologic data from an implantable cardiac function management device, the physiologic data resulting from operation of the implantable cardiac function management device using a plurality of therapy control parameter sets; means for analyzing the physiologic data; and means for selecting a particular therapy control parameter set using the analysis.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
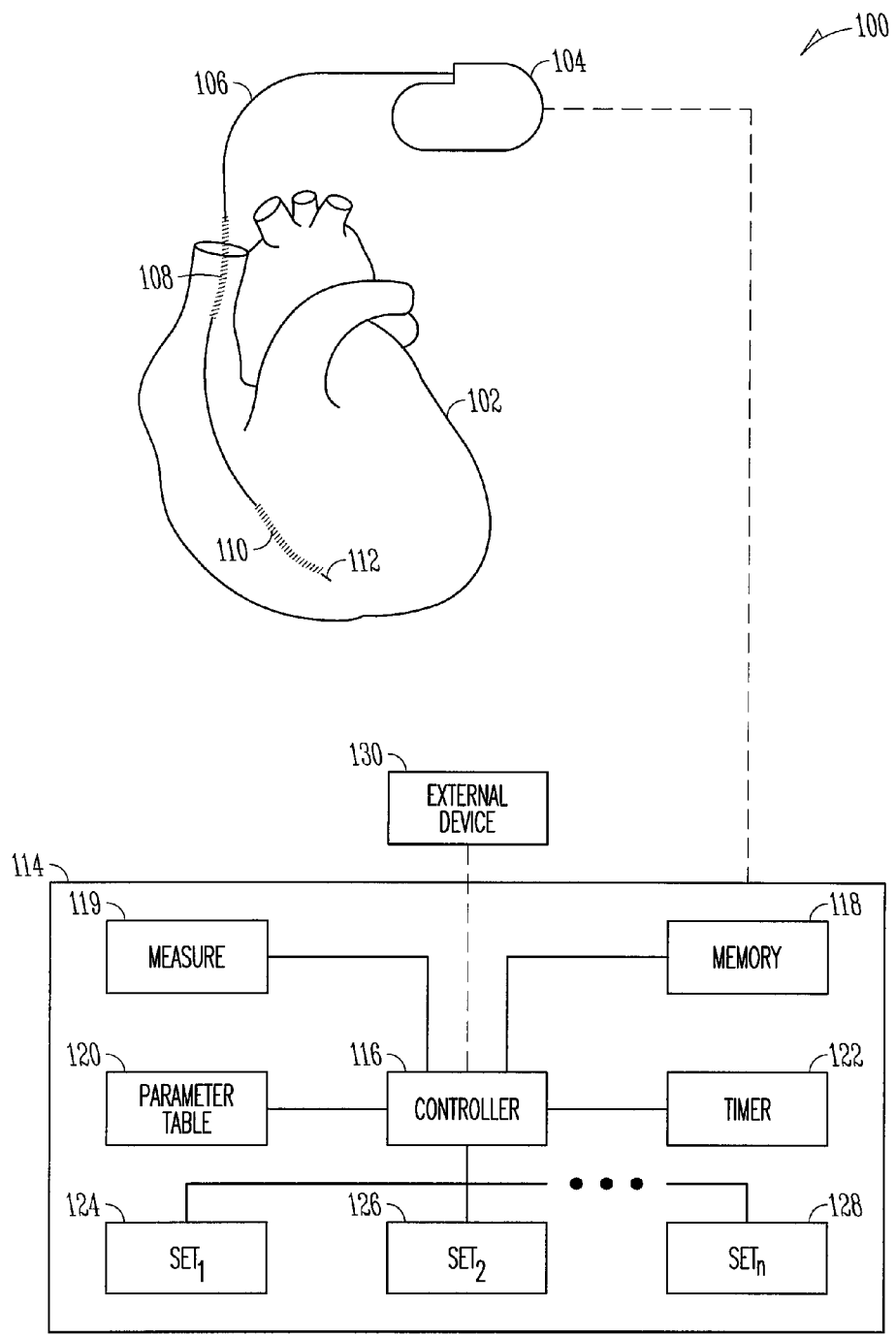
FIG. 1 illustrates an example of portions of a system which utilizes a device for monitoring and controlling electrical signals of the heart.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The present systems and methods are described with respect to implantable medical devices such as neurostimulation devices, gastrointestinal stimulation devices, retinal implants, cochlear implants and including CRM devices, such as pacemakers, cardiac function management devices (CFMDs), implantable cardioverter-defibrillators (ICDs), pacer-defibrillators, and single or multi-chamber cardiac resynchronization therapy (CRT) devices that use pacing. The device may also be programmed to monitor and store one or more measured physiological parameters using a given programmed parameter set. In certain examples, the programmed parameter set contains a single parameter adjusted among one or more values within a specified range. In another example, the programmed parameter set comprises multiple parameters adjusted among one or more values within a specified range. In certain examples, the programmed parameter set is determined as a function of one or more measured physiological parameters such as by use of an algorithm to calculate a value for use in at least one programmed parameter set. In certain examples, the device may identify safe limits such that an adverse condition would prompt a stop condition for at least one parameter set. The monitored or stored information may indicate information about the patient's response to a given parameter set and thereby can sometimes be used to determine an improved programmed parameter set. For example, one measured physiological parameter may indicate how the heart reacts during one or more specific activities that, when repeated, can identify a value for a programmed parameter set or determinable condition or outcome. In another example, a "target" physiological outcome may be specified, and the stored physiological information corresponding to a particular programmed parameter set may be compared against this target such as to determine whether any changes should be made to the programmed parameter set.

Each programmable parameter set may fit as part of a larger optimization program which uses ranges of parameter settings (e.g., AV delay range) and durations of each parameter set occurring in time (e.g., period of forty-eight hours). One example of this type of organization of variables uses a design of experiments (DOE). In DOE, a model, or series of models, can be developed to help determine what variables (e.g., parameter sets) affect a response of interest (e.g., % AV pacing). Using this method, one can determine certain variables, and can separate any dependent variables, which change in response to a change in one or more other variables, from any independent variables, which do not change in response to a change in one or more other variables. When only a few variables exist, the analysis may not need formal DOE, however, it is useful for a large number of variables or a complex interaction between variables. In certain examples, the automatic variation in one or more parameters, coupled with automatic analysis of one or more corresponding results obtained for different values of the one or more parameter, can be used to select (or to help a caregiver select) a set of parameter values that will produce a high probability of a desired response. This can reduce or eliminate clinician guess work and can obtain useful information about the effect of designed variations of one or more parameter values during the period of time between the implant of a device and the next patient follow-up, or between follow-ups. This can save time and allow much more information to be presented to the caregiver for tailoring the device for the patient.

Moreover, post-implant DOE techniques can provide data that will enable both caregivers and device manufacturers to explore performance variations resulting from parameter value variations. This information can be used to improve desirable patient outcomes earlier in the life of a particular model of device, for example. In certain examples, implanting a CRM device may involve programming a set of default parameter values based upon historical information about the subject's physiological condition before implantation. One or more parameter values can be controllably varied, and one or more specified indicators can then be monitored until the next follow-up between the caregiver and the subject. At that point, any recorded results may be reviewed by the caregiver, who may decide to modify one or more device parameter values, or automatically evaluated by the implanted device itself or by an ancillary external device. This may provide an early indication of the subject's response to a given therapy. Considering that a single programmed parameter set over the period of time (e.g., six months) provides a limited amount of information about the subject's response, the ability to provide multiple parameter sets occurring sequentially, or in combination, may provide significantly more valuable data for the caregiver or the device to evaluate.

FIG. 1 illustrates portions of a system 100 that uses a device 104 (e.g., implantable cardiac function management device), such as for monitoring one or more electrical signals of the heart 102. In certain examples, the device 104 may be coupled to one or more lead wires 106 having a first coil electrode 108, a second coil electrode 110, and a tip electrode 112, however, a leadless implementation is also possible. An electrogram signal (EGM) may be detected from one or more intrinsic electrical signals occurring within the heart 102, thereby providing information about heart contractions, such as an indication of heart rate, and information about how the values of the control parameters of the device 104 affect the rate. In this example, a control module 114 includes a programmable controller 116, which may be capable of performing several functions. In certain examples, programmable controller 116 may select a user-specifiable therapy control parameter value from a parameter table 120 as a result of receiving input from a user or caregiver. The parameter table 120 may contain a listing of one or more adjustable parameters, each having specified candidate values and a duration within which each such candidate value is to be applied. A specified range of a given control parameter may limit the candidate values of a particular parameter, such as by specifying a minimum value or maximum value.

For example, one possible therapy control parameter may include an atrioventricular (AV) delay that may have a specified range of possible candidate AV delay times that may be selected for a given parameter set. The AV delay may be associated with one or more parameter sets 124, 126 and 128. Each parameter set may include one or more user-specifiable therapy control parameters having a user-configurable range (or other specification of candidate values) and a user-configurable duration. For example, the duration of a specified candidate control parameter, within a particular parameter set, may include an associated period of time, such as forty eight hours, during which time a selected AV delay candidate value will be applied as part of a specified parameter set (e.g., 124, 126 or 128). A timer 122 may be used to count the duration for using a given parameter value or for using an entire parameter set (e.g., 124, 126 or 128). In certain examples, a parameter value will automatically switch from one value to another between parameter sets, such as to perform a DOE style variation in parameter values using the different parameter sets. In certain examples, the user-configurable duration may expire upon the measure module 119 reaching a threshold value. In certain examples, the device 104 cycles through various different parameter sets (e.g., 124, 126 or 128), such as during the period of time between an implant of the device 104 and a remote or local follow-up between a caregiver and the subject.

In the example of FIG. 1, an initial or first parameter set 124 ($SET_1$), may represent a first set of user-specified values and corresponding durations of specified device control or operating parameters from the parameter table 120. For example, the first parameter set 124 may list an AV delay parameter with a parameter value of 5 ms to be applied for a duration of forty-eight hours from a start to an end of a period during which the first parameter set 124 is in effect. Similarly, a second parameter set 126 ($SET_2$), may represent a second set of specified parameters from the parameter table 120. In certain examples the second parameter set 126, may be automatically put into effect upon the completion of a duration of the first parameter set 124 or of one or more durations of one or more specified therapy control parameters within a first parameter set 124. In yet another example, the second parameter set 126 may be automatically activated before the completion of the duration of the first parameter set 124, for example, upon measuring a response that meets a particular threshold value. The second parameter set 126 may automatically alter at least one parameter value from the first parameter set 124. A final parameter set 128 ($SET_N$), may represent the last parameter set among a number of specified parameter sets.

During the application of the various parameter sets, there may be one or more physiological measures collected by the measure module 119 to be stored within memory 118. The programmable controller 116 may obtain information about the one or more physiological measures in association with a combination of control parameter values in effect during a timer period when the physiological measure was obtained. Examples of one or more physiological measures to be monitored include but are not limited to heart rate, blood pressure, percent atrial or ventricular pacing, etc. A separate and unattached implantable or external physiological sensor may be used to obtain one or more physiological measures. Additionally, external device 130 may provide a physiological measure—and may interact with or operate independently of the programmed parameter sets. In certain examples, the external device 130 may include a weight scale, a blood pressure cuff, etc.

Figure 2:
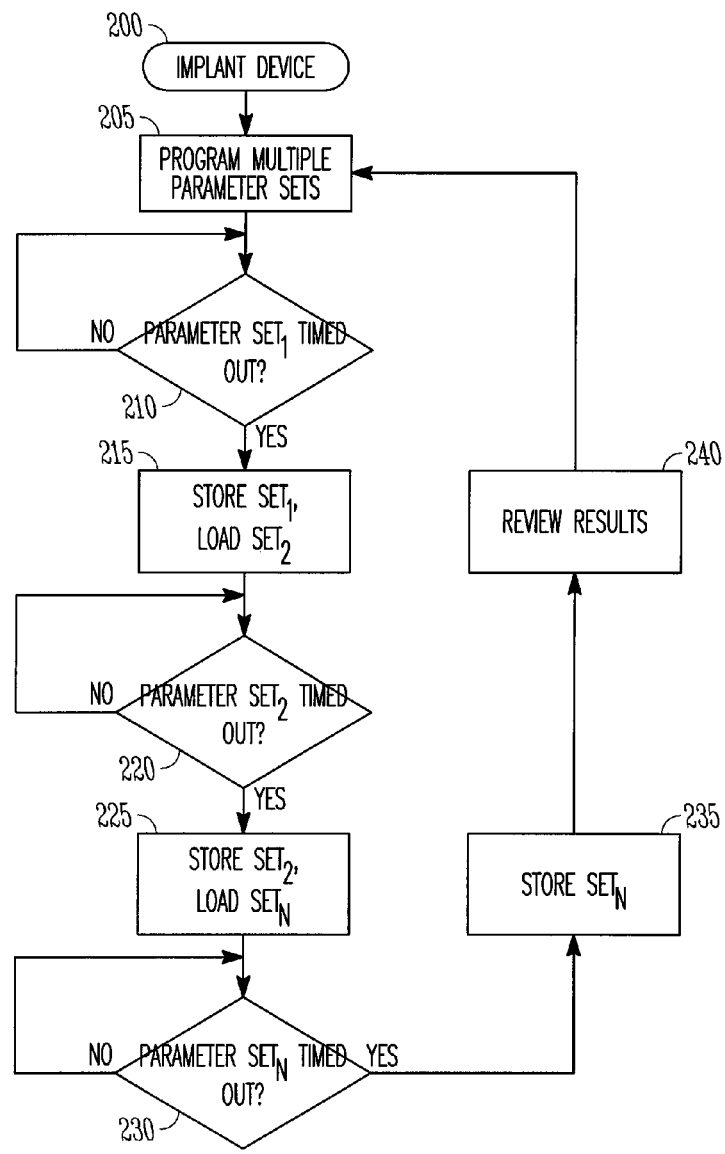
FIG. 2 is a flow chart illustrating generally an example of portions of a technique for programming multiple parameter sets and storing responses.

FIG. 2 is a flow chart illustrating generally an example of portions of a technique for programming multiple parameter sets and storing responses. In certain examples, the start of a programming cycle (or beginning of a first parameter set) follows the implant of an ICD or other implantable medical device. At 200, a device may be implanted within the body of a subject for monitoring intrinsic cardiac signals and, at 205, a control module (similar to control module 114 of FIG. 1) may be programmed with more than one parameter set ($SET_1, \ldots, SET_N$). In certain examples, a program may specify a first set of parameter values for first parameter set $SET_1$ and an associated duration. During at least a portion of the duration of the first parameter set $SET_1$, one or more physiological measures may be monitored and recorded.

At 210, the first parameter set $SET_1$ may be monitored for completion of its specified duration. If the duration has not yet reached completion, the control module 114 will continue to monitor. If however, at 210, duration of the first parameter set $SET_1$ has reached completion, at 215, the monitored potential outcome variables may be stored and associated with first parameter set $SET_1$ for later reference or retrieval. Additionally, at 215, the second parameter set $SET_2$ may be loaded by the control module 114 to begin the next phase of the programming cycle. In certain examples, the control module 114 may be programmed to delay the start of a subsequent parameter set for a specified duration, such as to establish a steady-state or reference condition before activating the next parameter set. In certain examples, this may involve returning to an interim parameter set between successive trial parameter sets. At 220, the second parameter set ($SET_2$) may be monitored for completion of its specified duration. Until its duration reaches completion, the control module 114 will continue to monitor and may record one or more specified outcome variables. Upon completion of the duration, at 225, the monitored potential outcome variables may be stored and associated with the second parameter set $SET_2$ for later reference or retrieval. At 215, the final parameter set $SET_N$ may be loaded by the control module 114 to begin the final phase of the programming cycle. At 230, duration of the final parameter set $SET_N$ is monitored by the control module 114 until completion of its duration. Upon completion of its duration, at 235, the monitored potential outcome variables may be stored. At 240, the caregiver may review the results associated with one or more parameter sets ($SET_1, \ldots, SET_N$). The caregiver may then use this information to choose, at 205, a parameter set for subsequent operation, or to create another DOE of multiple parameter sets to be executed before another follow-up.

Figure 3:
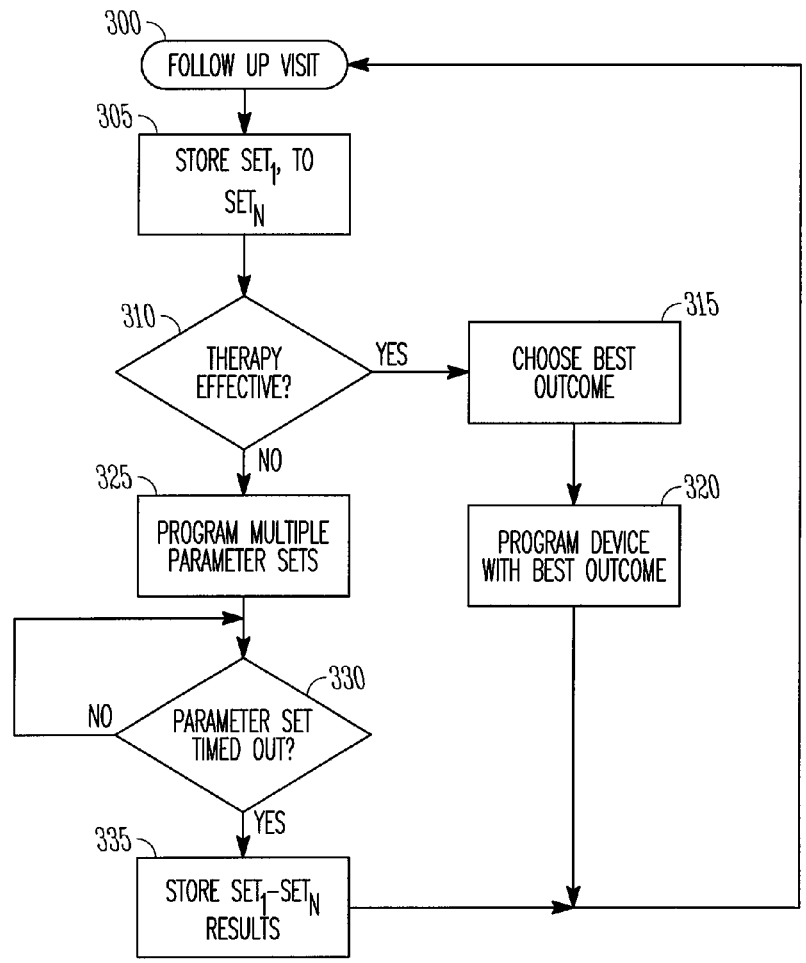
FIG. 3 is a flow chart illustrating generally an example of how the results of the multiple parameter sets are evaluated and revised, such as for optimization.

FIG. 3 is a flow chart illustrating generally an example of how the monitored results of the multiple parameter sets can be evaluated and parameter values improved or optimized, such as that performed at 240 of FIG. 2. At 300, a follow-up may be scheduled to review the results obtained from the one or more parameter sets ($SET_1, \ldots, SET_N$). At 305, the stored results may be evaluated to determine if a change in one or more programmed parameter values is warranted, or if further monitoring of results for different parameter sets is warranted. The caregiver may choose to have the information presented in a trended or other graphical representation to better represent the connection between a particular parameter set (or chosen therapy) and a corresponding monitored physiological measure. At 310, the caregiver may make a determination as to the effectiveness of the applied therapy (associated with the corresponding parameter sets). The therapy may be deemed effective if one or more parameter sets caused a desired outcome in one or more monitored physiological measures. If the caregiver determines that the therapy was effective (e.g., best outcome reached), at 315, the identified one or more control parameter values are chosen from the one or more parameter sets ($SET_1$-$SET_N$) and at 320, the control module 114 may be programmed to use the chosen parameter values for a subsequent specified duration or indefinitely, during which time the control module 114 may continue to monitor one or more physiological measures, if the user desires. Upon completion of the best outcome duration, at 300, a follow-up may occur.

If, at 310, the caregiver determines that the therapy was not effective, then at 325, one or more programmed parameter sets can be revised, such as for further experimentation and monitoring. At 330, the one or more parameter sets ($SET_1$, ..., $SET_N$) are monitored until their durations have completed, thereafter, at 335, the results associated with physiological measures are stored. At 300 a follow up is carried out.

Figure 4:
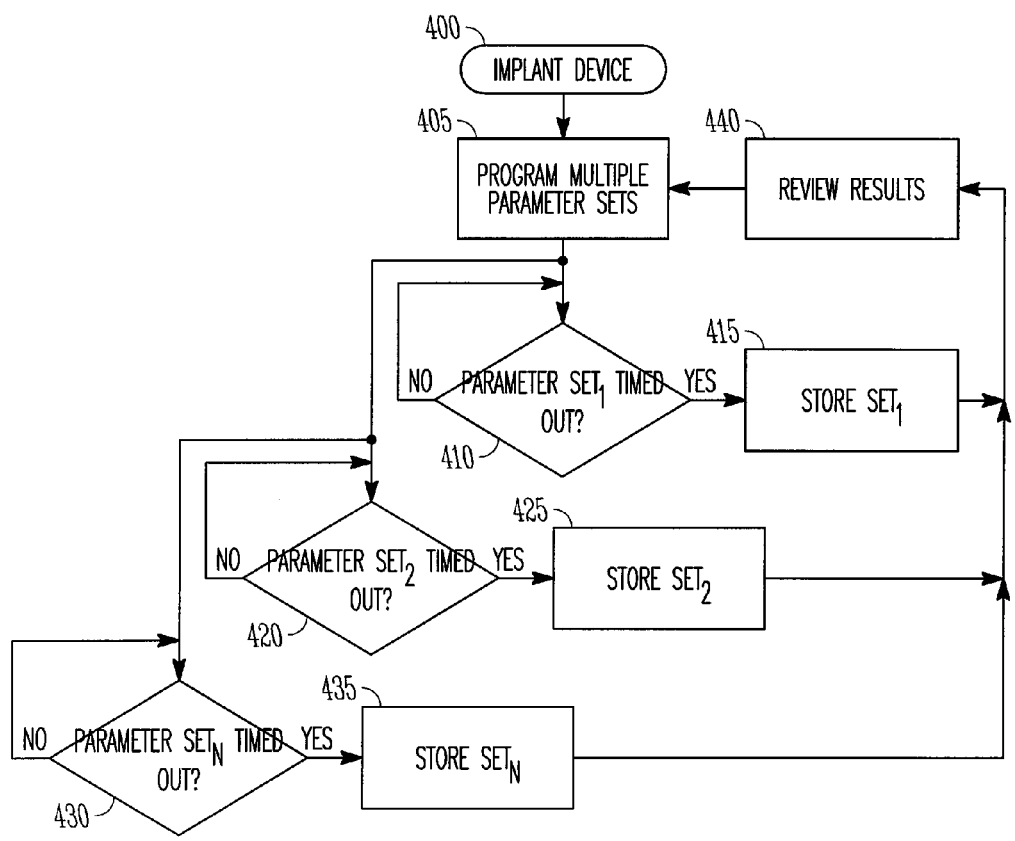
FIG. 4 is a flow chart illustrating generally an example of how multiple parameter sets may operate concurrently.

DOE permits understanding of the effect that each variable has on a given system. As a result, multiple parameters may be concurrently varied in value, and DOE techniques used to extract the impact of a particular parameter on the resulting monitored physiological output variable. FIG. 4 is a flow chart illustrating generally an example of how multiple parameter sets may operate concurrently. At 400, a device may be implanted within the body of a subject for monitoring intrinsic cardiac signals. At 405, a control module 114 (similar to control module 114 of FIG. 1) may be programmed with more than one parameter set ($SET_1$, ..., $SET_N$). In certain examples, one or more parameter sets such as first parameter set $SET_1$ 410, second parameter set $SET_2$ 420 and final parameter set $SET_N$ 430 may occur concurrently or be subject to overlap of varying durations. The control module 114 may monitor physiological measures for each parameter set in combination or separately until each has completed its duration. Upon completion of the duration of the first parameter set $SET_1$ 410, second parameter set $SET_2$ 420 and final parameter set $SET_N$ 430, the control module 114 will store the monitored results at 415 ($SET_1$), 425 ($SET_2$) and 435 ($SET_N$), respectively. At 440, all of the results are reviewed by the caregiver at the next follow-up visit with the subject.

Figure 5:
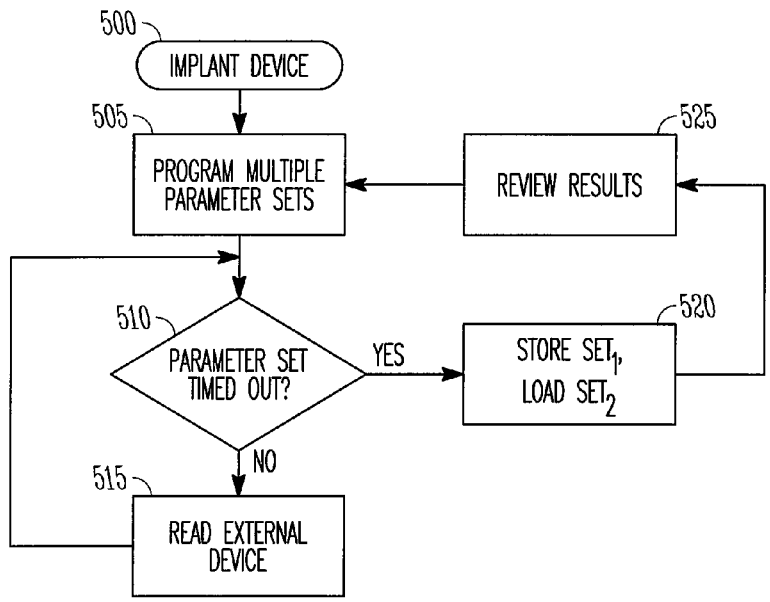
FIG. 5 is a flow chart, similar to FIG. 2, but illustrating an example of a technique in which an external device parameter is read as part of the programmed parameters.

In certain examples, the control module 114 may collect information from an external device 130 to be used as part of the therapy for the subject and as a variable to be analyzed with the implantable cardiac rhythm management device and related specified parameter sets. In FIG. 5, the caregiver may implant an implantable cardiac rhythm management device at 500 and, at 505, one or more programmable parameter sets may be programmed with a one or more parameters having a range or varying values and a duration. At 510, the control module 114 waits for the parameter set's duration to elapse. In certain examples, the control module 114 recurrently or periodically checks for a completed duration and initiates a read operation to obtain updated information from the external device 515, e.g., just before such completion. At 520, the duration of one or more parameter sets has reached completion, and the monitored physiological measures may be stored and associated with the particular parameter set for future reference or retrieval. At 520, any remaining parameter sets may be loaded by the control module 114 to begin the next phase of the programming cycle. At 525, the results may be reviewed by a caregiver at a follow-up, such as before repeating a new cycle of parameter sets.

In certain examples, a caregiver may indicate a desired outcome or target value for a particular physiological measure, in anticipation of reaching the target value during implementation of one or more control parameters or among one or more parameter sets. In certain examples, one or more quantitative criteria based upon one or more monitored physiological parameters may prompt the control module 114 to select one or more parameter sets. For example, a system 100 may include one or more sensors to measure right and left ventricular pressure and a target value that can be specified by a user or caregiver. In certain examples, this target value may represent an increase in ventricular pressure over time (dP/dt), an increase in stroke volume, or a decrease in mechanical dyssynchrony. In such examples, the control module 114 may determine which parameter set resulted in reaching the target value and may further select a next parameter set based upon this determination. In such cases, there may be a need to store a target result within the control module 114 and later compare a monitored result to the target value. The target may be representative of one or a combination of multiple physiological measures. Similarly, the control module 114 may be configured to identify which parameter set produces a target result and to store that information. For example, this may include identifying and storing the parameter set associated with the largest increase in ventricular pressure or a largest decrease in mechanical dyssynchrony.

Figure 6:
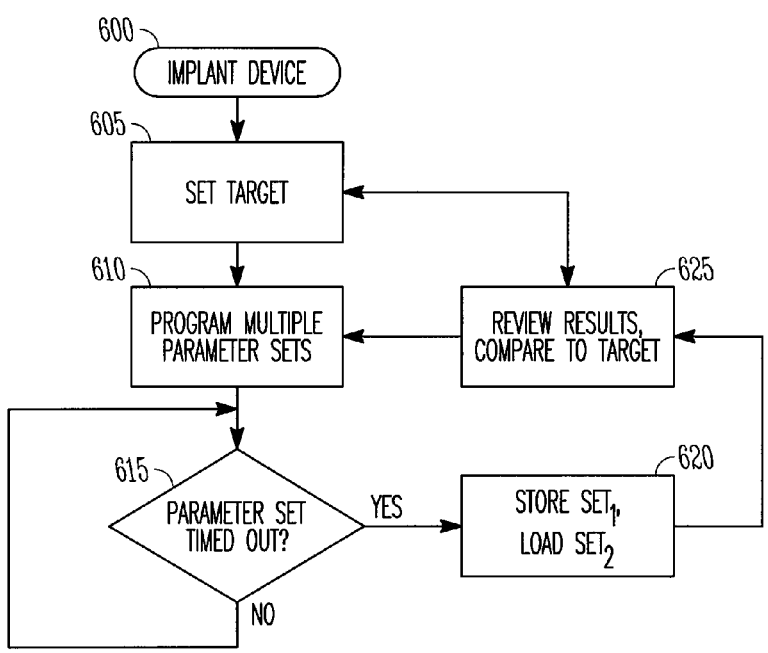
FIG. 6 is a flow chart of an example, similar to FIG. 2, in which the implantable cardiac function management device includes a target outcome which is later compared against the results.

In FIG. 6, at 600, the caregiver implants an implantable cardiac device within the body of a subject. At 605, the caregiver specifies a target value for one or more physiological measures. At 610, the control module 114 may be programmed with one or more parameter sets, as discussed above. At 615, one or more physiological quantities corresponding to a parameter set may be monitored by the control module 114 until a completed duration is reached. At such time, at 620, the monitored results may be stored by the control module 114. Then, at 625, the results of at least one parameter set associated with past physiological measures may be reviewed and compared against the one or more targets at 605. At 610, the next parameter set may be loaded, or alternatively, based upon the comparison of the results from the prior parameter set, a modified parameter set may be programmed by the control module 114 to run next. In this manner, the caregiver may have a specified range within which the program may operate and refine a parameter set with the goal of reaching a specified target without additional follow-ups. Alternatively, a proposed set of parameter settings may be suggested at 610, to be reviewed by the caregiver at the next follow-up. In certain examples, the device may use one or more search techniques to explore measured physiological parameters and improve or optimize a programmed parameter set. For example search techniques may include, but are not limited to hill climbing, genetic search, heuristic search, A\* ("A star" search, simulated annealing, or minmax).

Figure 7:
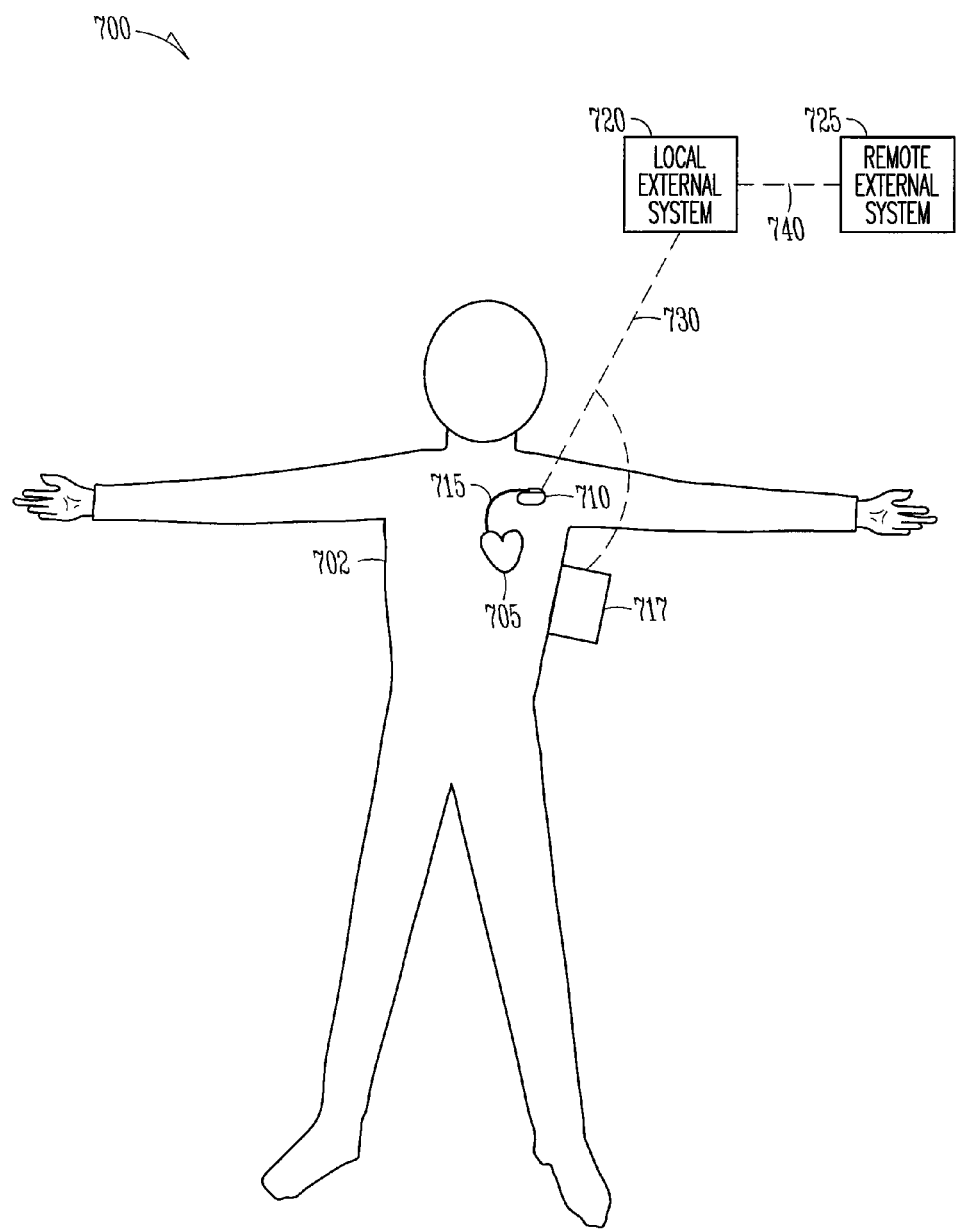
FIG. 7 illustrates an example of an implantable medical device in telemetric communication with a local external system and a remote external system.

FIG. 7 is a block diagram illustrating an example of a medical device system 700, and portions of an environment in which it is used. The environment includes a body 702 with a heart 705. In this example, system 700 can include an implantable medical device 710, a lead system 715, an external sensor device 717, a local external system 720, and a remote external system 725. The local external system 720 is coupled to the implantable medical device 710 via a telemetry link 730, and the remote external system 725 is coupled to the local external system 720 via a telemetry link 740. The external sensor device 717 senses electrical, vibration, or other physiological information from the body 702. The external sensor device 717 is coupled to the local external system 720 via telemetry link 730.

Figure 8:
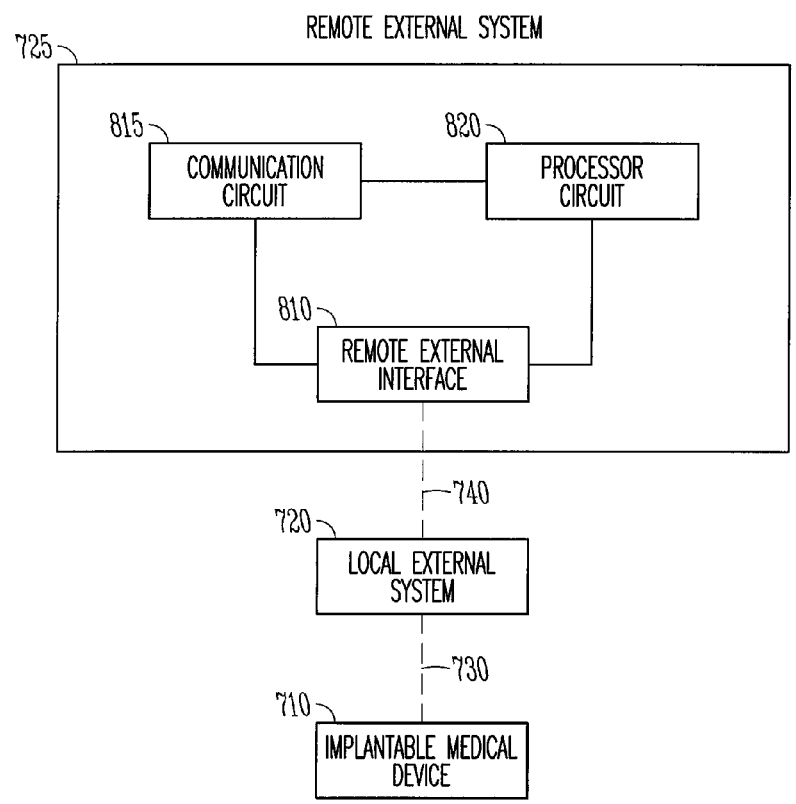
FIG. 8 illustrates an example in block diagram form of a remote external system in telemetric communication with a local external system and an implantable medical device.

FIG. 8 illustrates an example of the remote external system 725 including a remote external interface 810. The remote external interface 810 can include one or more of a processor, a server, and a display unit. The remote external interface 810 is configured to be coupled to the implantable medical device 710 via the communication link 740 (such as a wireless link or a network connection) to the local external interface or system 720, and via the telemetry link 730 between the local external interface 720 and the implantable medical device 710. The remote external system 725 can include a communication circuit 815 and a processor circuit 820.

The communication circuit 815 is configured to communicate with the implantable medical device 710. This communication can be in real time. As noted above, this communication can use the links 730 and 740 and the local external interface 720. The processor circuit 820 is configured to perform an analysis of physiologic data that is received from the implantable medical device 710. This data is captured by the implantable medical device 710 in response to operation of the implantable medical device 710 using a plurality of therapy control parameter sets. The processor circuit 820 is further configured to select a particular therapy control parameter set based on its analysis of the physiologic data.

In an example, a particular therapy control parameter set may include one or more of an AV delay parameter, a VV offset parameter, a rate response parameter, a tachy detection parameter, a tachy therapy parameter, a pacing amplitude parameter, or a neural stimulation parameter. The rate response parameter can include an activity threshold, a reaction time, a recovery time for an accelerometer-based method, and a response factor for a minute ventilate-based method. The reaction time relates to the time period between a sensed need for pacing and an initiation of the pacing. Similarly, the recovery time relates to the time period between when the pacing is no longer needed and the cessation of the pacing. The tachy detection parameter can include a tachy rate detection zone threshold and a tachy detection enhancement. Some pacers include multiple tachy rate detection zone thresholds (expresses as beats per minute) that are identified as different tachy conditions. A tachy detection enhancement relates to the determination of arrhythmias as being from the atrium or the ventricle, and using this information to determine if the detected arrhythmia is of concern. The tachy therapy parameter can include a shock energy level or an anti-tachy pacing (ATP) scheme. The physiologic data received by the remote external interface 725 can include one or more of a heart rate, a heart rate variability, a peripheral pressure, a blood pressure, a body weight, an activity log, a tachy conversion efficacy, a respiration rate, a posture indicator, a hemodynamic response parameter, an electrocardiogram, or a percentage of atrial or ventricular pacing.

A dual sensor adaptive-rate pacing system, such as one with an accelerometer and a minute ventilation sensor, typically requires a parameter search of response factors for both of the sensors. Given that each sensor may have a range of response factor settings, for example 1 through 16 for both sensors, the combinations of the parameter settings rise to 256 possibilities, providing a difficult task for a clinician to accomplish. However, using one of the parameter search algorithms, such as a gradient search, an evolution algorithm, a simulated annealing method, or a simplex algorithm, only a limited combination are needed to reach an optimal response factor combination for the two sensors.

In an example of optimizing AV delay and VV delay settings for bi-ventricular pacing, both delay settings have a range of timing intervals that can be programmed. A parameter search algorithm can be used with consideration of patient response through measurements from both internal or external sensors. A convergence to the optimal combination of AV and VV delay settings can be found more quickly than the step-wise search through every possible combination of the two parameters.

Figure 9:
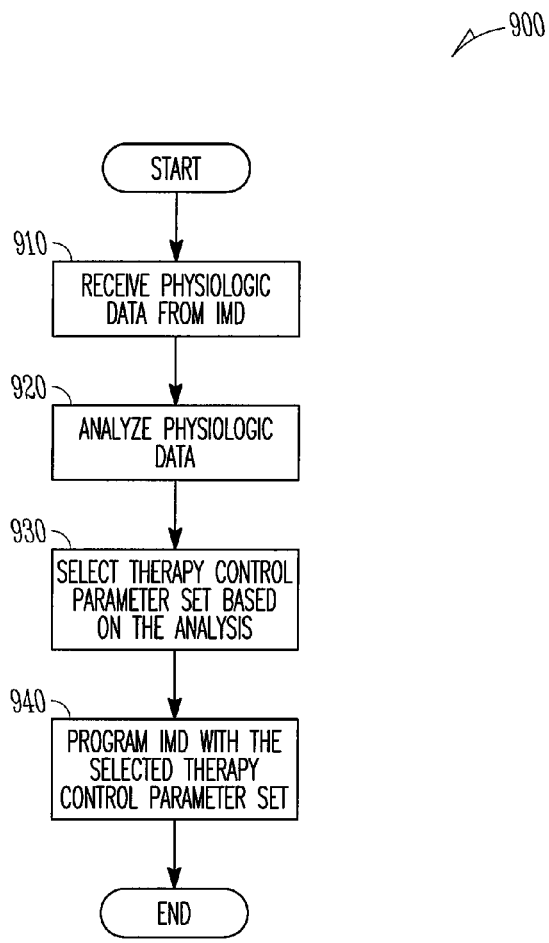
FIG. 9 illustrates an example process to program an implantable medical device with a therapy control parameter set.

FIG. 9 illustrates an example of a process 900 to program an implantable medical device with a particular therapy control parameter set. At 910, physiologic data is received from an implantable medical device. The physiologic data can be transmitted from an implantable medical device such as device 710 through a network such as the local external system 720, the telemetry links 730 and 740, and received at the remote external system 725. The physiologic data can result from operation of the implantable medical device using a plurality of therapy control parameter sets. At 920, the physiologic data is analyzed. This analysis can be performed by a processor such as processor circuit 820. At 930, the processor circuit selects one of the particular therapy control parameter sets based on its analysis of the plurality of the sets. At 940, the implantable medical device is programmed with the particular therapy control parameter set selected by the processor circuit.

Figure 10:
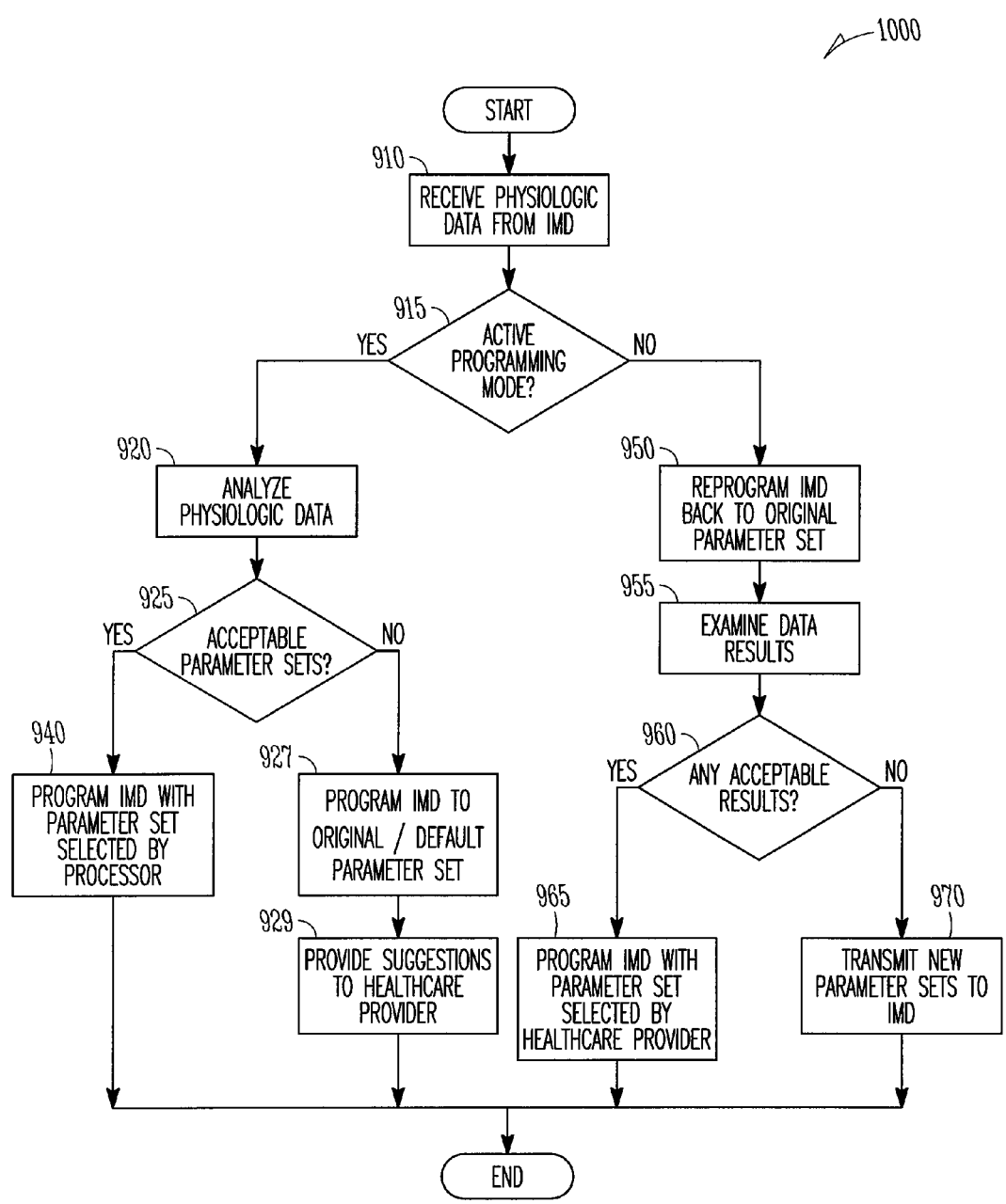
FIG. 10 illustrates another example process to program an implantable medical device with a therapy control parameter set.

FIG. 10 illustrates another example of a process 1000 to program an implantable medical device with a particular therapy control parameter set. As in process 900 of FIG. 9, physiologic data is received at 910. At 915, a check is made to determine if the system is set for an active programming mode. If the system is set for active programming mode, then at 920, the physiologic data is analyzed. In an example, device performance data or patient feedback data can also be analyzed. For example, if a patient indicates that he did not feel well when a particular therapy control parameter set was in place and executing, then a health care provider can decide not to use that therapy control parameter set again. At 925, the processor circuit determines if one or more of the therapy control parameter sets are acceptable. If the processor circuit determines that one or more therapy control parameter sets are acceptable, then at 940, the implantable medical device is programmed with the particular therapy control parameter set selected by the processor circuit. If the processor circuit determines at 925 that none of the therapy control parameter sets are acceptable, then at 927, the implantable medical device is programmed to its original or default therapy control parameter set. At 929, a health care provider is informed of the results, and suggestions are provided to the health care provider. An example suggestion would be to change a particular parameter in the parameter set to a certain value, and resubmit the altered parameter set to the implantable medical device via the remote external system 725.

At 915, if the processor circuit determines that the system is not set to an active programming mode, then at 950, the device is first reprogrammed back to its original therapy control parameter set. At 955, a health care provider examines the data resulting from the use of the plurality of therapy control parameter sets. At 960, the health care provider determines if any of the plurality of therapy control parameter sets produced acceptable results. If the health care provider determines that one or more therapy control parameter sets produced acceptable results, than at 965, the health care provider programs the implantable medical device with his or her choice of a therapy control parameter set. This determination can be based on one or more suggestions or other information provided by the remote external system 725. Such suggestions can be based on the patient's historic data maintained at the remote external system, or an aggregation of historic data from a plurality of patients. If no acceptable results are found, then at 970, a new plurality of therapy control parameter sets can be transmitted to the implantable medical device. The new therapy control parameter sets can be provided by the health care provider via the remote external interface 810, and may or may not be based on suggestions provided by the remote external system 725.

In connection with the processes 900 and 1000, a health care provider can provide an interval range for one or more parameters in a parameter set. This can be input at the remote external interface 810. A health care provider can also provide at the remote external interface 810 a time interval that the implantable medical device can operate with at least one of the therapy control parameter sets. A health care provider can also provide a particular value for a physiological parameter in the therapy control parameter set.

In an example, the processor circuit 820 can adjust a parameter search space based on the analysis of the physiologic data. For example, the A-V delay can be altered based on the results generated with other known values of the A-V delay. The parameter search space can be adjusted using one or more of a gradient search, an evolution algorithm, a simulated annealing method, or a simplex algorithm.

Figure 11:
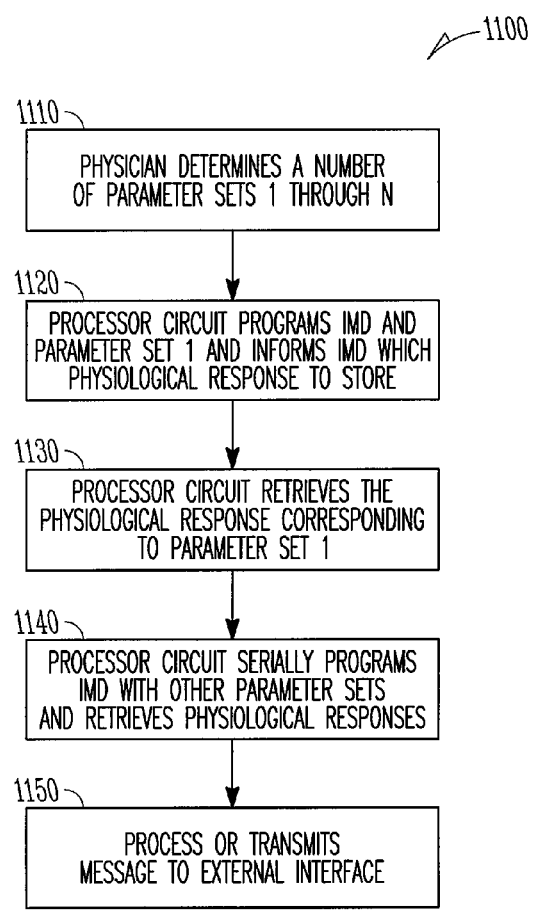
FIG. 11 illustrates another example process to program an implantable medical device with a therapy control parameter set.

FIG. 11 illustrates another example process 1100 to program an implantable medical device with a therapy control parameter set. At 1110, a physician determines a number of parameter sets 1 through N (or a range of a parameter to be evaluated) to be used in the implantable medical device. In an example, the external interface can provide to a physician one or more recommended parameter sets to be investigated based on data from a large patient data base. At 1120, the processor circuit on the remote external system programs the implantable medical device with the parameter set 1, and informs the implantable medical device which physiological response to monitor and store. The processor circuit can also perform an analysis of the physiological response and adjust the parameter sets accordingly. The processor circuit can also serve as storage of the physiological responses for different parameter sets. The physician can make the decision as to what parameter set to use. At 1130, the processor circuit retrieves the physiological response corresponding to the parameter set 1 via the communication circuit. The retrieval of these physiological responses can be performed at physician-determined intervals. At 1140, the processor circuit serially programs the implantable medical device with the other parameter sets, and retrieves the physiological responses generated during the device operation with each of these parameter sets. At 1150, the processor circuit analyzes the physiological response and selects a particular parameter set as a preferred configuration for the implantable medical device. At 1150, the processor transmits a message to the external interface informing a physician that the results are ready for review.

Figure 12:
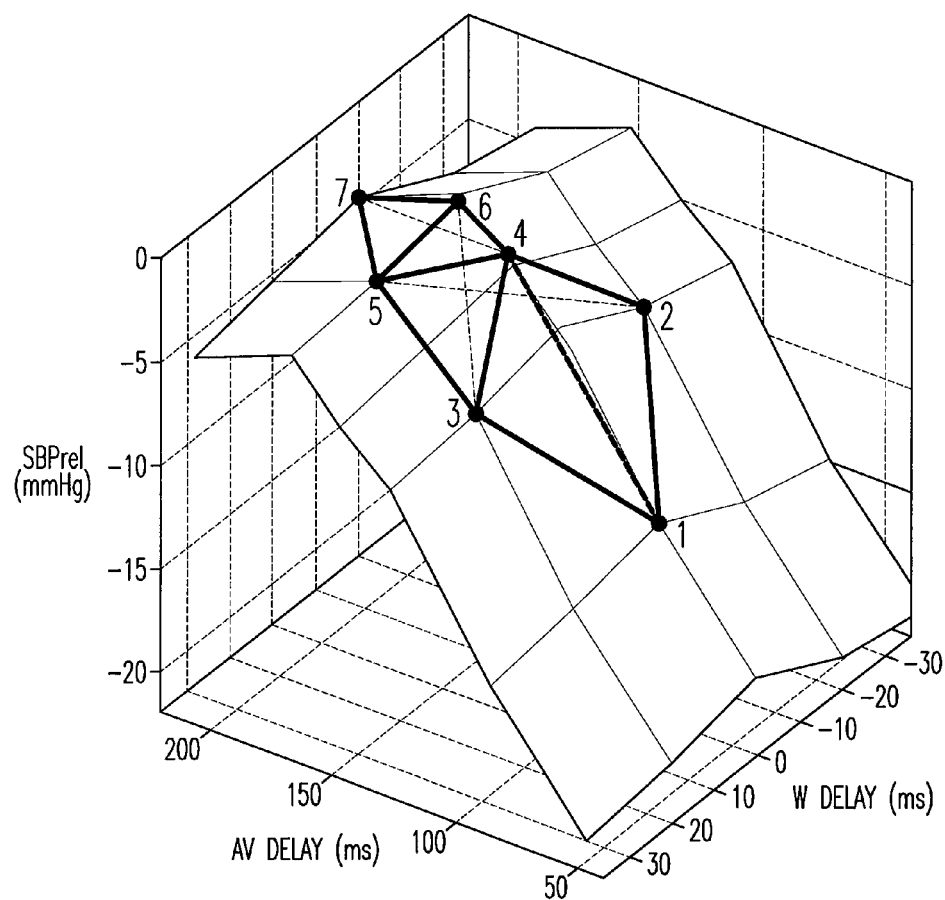
FIG. 12 is a graph illustrating an example of a process to reduce search parameter sets for CRT optimization.

FIG. 12 is a graph illustrating an example of a process to reduce a search parameter space for CRT optimization. A search parameter space can include a number of parameter sets or a number of parameters and parameter values within one or more parameter sets. Referring specifically to FIG. 12, for CRT AV and VV delay optimization, to reach optimized value, all combinations of AV and VV delay need to be examined. In FIG. 12, 6 AV delay and 5 VV delays are investigated. This results in a total of 30 possible AV and VV combinations. However, by using optimization algorithms, the search parameter sets can be significantly reduced. The simplex optimization algorithm is used as an example in FIG. 12.

First, 3 AV and VV combinations within a physician determined range are chosen by the processor circuit. The physiological response, in this case, blood pressure ($SBP_{rel}$ (mmHg)), corresponding to each of the 3 AV and VV combinations (point 1, 2, 3 on FIG. 12) is measured. In FIG. 12, the AV and VV combination at point 1 produces the least desirable response. A new parameter set 4 is then generated by reflection into the parameter space opposite the undesirable result. Similarly, parameter set 5 is generated by comparing the response from AV and VV combinations at points 2, 3, and 4, and reflecting into the parameter space opposite the least desirable combination at point 2. Then parameter set represented by point 6 is generated by comparing a response from parameter sets at points 3, 4, and 5, and the physiological response from the parameter set at point 6 is collected. The parameter set at point 7 is then chosen based on comparing the responses from parameter sets at points 4, 5, and 6, and reflecting into the parameter space opposite the least desirable parameter set, that is, set 4. The physiological response from the parameter set at point 7 is then collected. However, since the physiological response from the parameter set at point 7 does not exceed that of the parameter set at point 6, the search is stopped and the parameter set at point 6 is chosen as the optimal AV and VV combination. From this example, it can be seen that by using optimization algorithms, the parameter search sets can be significantly reduced, from 30 to 7 in this example.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72(b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. An apparatus comprising:
    an implantable cardiac function management device including a programmable controller, the programmable controller configured to include a plurality of user-specifiable therapy control parameter sets, wherein a therapy control parameter set is configured to include at least one of a rate response parameter, a tachy detection parameter, and a tachy therapy parameter, and wherein the programmable controller is configured to initiate a switch from a first therapy control parameter set to a second therapy control parameter set upon expiration of a user-configurable time duration; and a remote external interface for the implantable cardiac function management device, configured to be communicatively coupled to the implantable cardiac function management device via a network to a local external interface and via telemetry between the local external interface and the implantable cardiac function management device, the remote external interface comprising:

a communication circuit, configured to communicate with the implantable cardiac function management device; and a processor circuit, configured to perform an analysis of physiologic data received from the implantable cardiac function management device in response to operation of the implantable cardiac function management device using a plurality of the therapy control parameter sets, the processor circuit configured to select a particular therapy control parameter set using the analysis, wherein at least one of the implantable medical device or the processor is configured to analyze physiologic data resulting from using the first therapy control parameter set and to generate a search set of candidate values of a therapy parameter for the second therapy parameter set or a subsequent parameter set by reducing a set of possible values to the search set of candidate values according to the analyzed physiological and previous values of the therapy parameter set used to produce the physiologic data.

2. The apparatus of claim 1, wherein the controller is configured to obtain at least one physiological measure for each combination of parameter values of the therapy control parameter set.

3. The apparatus of claim 2, wherein the at least one physiological measure includes information from a separate and unattached physiological sensor.

4. The apparatus of claim 2, wherein the controller is configured to determine which combination of parameter values contributed to a particular outcome as evidenced by at least one physiological measure.

5. The apparatus of claim 4, wherein the controller is configured to determine which of the first and second parameter values contributed more to the at least one physiological measure.

6. The apparatus of claim 4, wherein the controller is configured to suggest at least one combination of parameter values as a function of past physiological measures.

7. The apparatus of claim 1, wherein the device includes multiple therapy control parameter sets, and wherein the device is configured to sequence through two or more of the therapy control parameter sets.

8. The apparatus of claim 1, comprising one or more of the implantable cardiac function management device, the local external interface, and an external sensor device.

9. The apparatus of claim 1, wherein the remote external interface is configured to program the implantable cardiac function management device with one or more of the particular therapy control parameter sets and a particular physiological response to store.

10. The apparatus of claim 1, wherein the remote external interface is configured to program the implantable cardiac function management device with an original therapy control parameter set or a default therapy control parameter set.

11. The apparatus of claim 1, wherein the local external interface, the network, or the remote external interface is configured to suggest to a third party the particular therapy control parameter set to program into the implantable cardiac function management device.

12. The apparatus of claim 11, wherein the suggestion is based on at least one of an analysis of an aggregation of historic patient data or device performance data.

13. The apparatus of claim 1, wherein the processor circuit is configured to perform an analysis of at least one of device performance data or patient feedback data.

14. The apparatus of claim 1, wherein the processor circuit is configured to adjust one or more therapy control parameter sets using the analysis of the physiologic data.

15. The apparatus of claim 14, wherein the adjustment of the one or more therapy control parameter sets comprises using the analysis of the physiologic data to reduce a parameter space for which the processor circuit then analyzes the physiologic data.

16. The apparatus of claim 15, wherein the optimization algorithm includes at least one of a gradient search, an evolution algorithm, a simulated annealing method, or a simplex algorithm.

17. The apparatus of claim 1, wherein:
the rate response parameter includes at least one of an activity threshold, a reaction time, a recovery time for an accelerometer-based method, and a response factor for a minute ventilate-based method;
the tachy detection parameter includes at least one of a tachy detection zone threshold and a tachy detection enhancement; and
the tachy therapy parameter includes at least one of a shock energy level or an anti-tachy pacing (ATP) scheme.

18. A method comprising:
receiving user input to program an implantable cardiac function management device including receiving a plurality of therapy control parameter sets, a therapy control parameter set including at least one of a rate response parameter, a tachy detection parameter, or a tachy therapy parameter;
initiating, using the implantable cardiac function management device and upon expiration of a user-configurable time duration, a switch from a first therapy control parameter set to a second therapy control parameter set;
analyzing, using at least one of the implantable medical device or a remote external interface, physiologic data resulting from using the first therapy control parameter set;
generating, using the at least one of the implantable medical device or the external interface, a search set of candidate values of a therapy parameter for the second therapy parameter set or a subsequent parameter set according to the analyzed physiological data, wherein the search set of candidate values are reduced from a set of possible values according to the analyzed physiological data and previous values of the therapy parameter set used to produce the physiologic data;
receiving over a network at the external interface physiologic data from the cardiac function management device, the physiologic data resulting from operation of the cardiac function management device using a plurality of the therapy control parameter sets;
analyzing the physiologic data resulting from using the plurality of therapy control parameter sets; and
selecting a particular therapy control parameter set using the analysis.

19. The method of claim 18, comprising obtaining at least one physiological measure for each combination of parameter values of the therapy control parameter set.

20. The method of claim 18, comprising determining which of the combination of parameter values contributed to a particular outcome as evidenced by at least one physiological measure.

21. The method of claim 18, comprising using the user input for automatically sequencing through multiple therapy control parameter sets at times occurring between separate user-programming sessions.

22. The method of claim 18, comprising programming the implantable cardiac function management device with the particular therapy control parameter set.

23. The method of claim 18, comprising providing to a third party a suggestion of the particular therapy control parameter set to program into the implantable cardiac function management device.

24. The method of claim 18, comprising automatically adjusting the particular therapy control parameter set or a particular therapy control parameter and automatically programming the adjusted particular therapy control parameter set or the particular therapy control parameter into the implantable cardiac function management device.

25. The method of claim 18, comprising receiving, at the remote external interface, from a third party, the one or more therapy control parameter sets.

26. The method of claim 18, comprising receiving, at the remote external interface, an interval range for at least one parameter in the therapy control parameter sets, a time interval that the cardiac function management device is configured to operate with at least one of the therapy control parameter sets, or a value for a physiological parameter.

27. The method of claim 18, comprising adjusting the therapy control parameter sets using the analysis of the physiologic data.

28. The method of claim 18, comprising using the analysis of the physiologic data to reduce a parameter space in which the physiologic data is then analyzed.

29. The method of claim 18, wherein
the rate response parameter includes at least one of an activity threshold, a reaction time, a recovery time for an accelerometer-based method, and a response factor for a minute ventilate-based method;
the tachy detection parameter includes at least one of a tachy detection zone threshold and a tachy detection enhancement; and
the tachy therapy parameter includes at least one of a shock energy level or an anti-tachy pacing (ATP) scheme.

* * * * *